United States Patent [19]

DuPont

[11] Patent Number: 4,915,697
[45] Date of Patent: Apr. 10, 1990

[54] HYPODERMIC NEEDLE ASSEMBLY

[76] Inventor: Frank DuPont, 4495 Clarke Dr., St. Clair, Mich. 48079

[21] Appl. No.: 339,960

[22] Filed: Apr. 18, 1989

Related U.S. Application Data

[63] Continuation of Ser. No. 170,680, Mar. 16, 1988, abandoned, which is a continuation of Ser. No. 33,657, Apr. 3, 1987, abandoned.

[51] Int. Cl.⁴ ............................................. A61M 5/32
[52] U.S. Cl. .................................... 604/192; 604/198; 604/263
[58] Field of Search ............... 604/187, 198, 192, 263, 604/110

[56] References Cited

U.S. PATENT DOCUMENTS

| | | | |
|---|---|---|---|
| 268,996 | 12/1882 | Brinkerhoff | 604/198 |
| 2,674,246 | 4/1954 | Bower | 604/198 |
| 2,847,995 | 8/1958 | Adams | 604/198 |
| 2,888,924 | 6/1959 | Dunmire | 604/198 X |
| 3,134,380 | 5/1964 | Armao | 604/198 |
| 4,507,118 | 3/1985 | Dent | 604/198 |
| 4,564,054 | 1/1986 | Gustausson | 604/198 X |
| 4,775,369 | 10/1988 | Schwartz | 604/263 |
| 4,795,432 | 1/1989 | Karczmer | 604/110 |

*Primary Examiner*—John D. Yasko
*Attorney, Agent, or Firm*—Krass and Young

[57] ABSTRACT

A needle assembly especially suited for hypodermic syringe use in which an axially collapsible sleeve is positioned over the needle. The sleeve includes an upper axially rigid portion sized to mount over the base portion of the needle, an axially collapsible intermediate portion, and an axially rigid lower portion defining a central bore sized to telescopically receive and protect the lower pointed end of the needle. In use, the sleeve selectively collapses axially as the needle enters the subject so that the point of the needle is never exposed during insertion, and selectively extends axially during withdrawal of the needle so that again the pointed tip of the needle is never exposed.

21 Claims, 1 Drawing Sheet

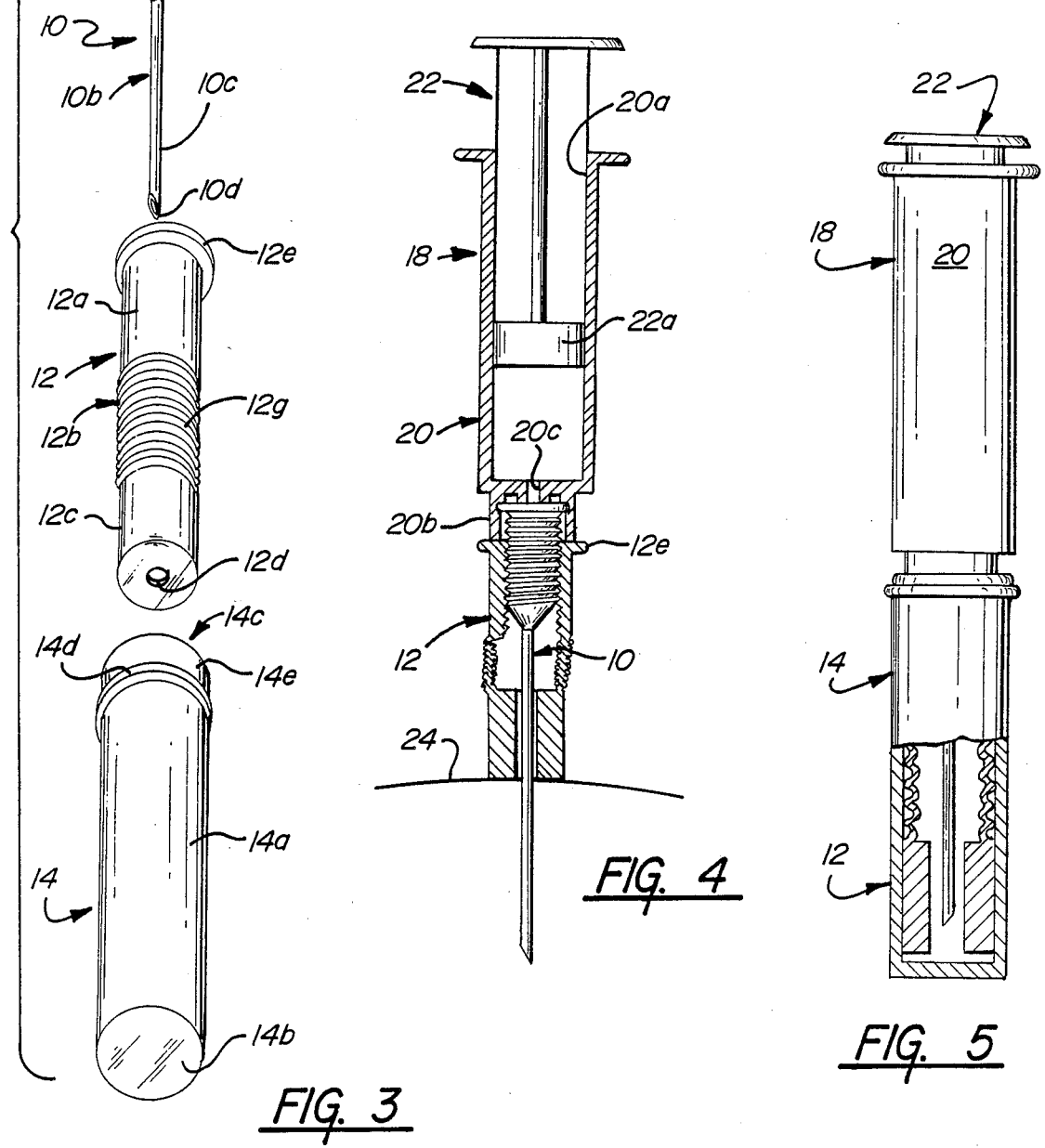

HYPODERMIC NEEDLE ASSEMBLY

This is a continuation of application Ser. No. 170,680 filed on Mar. 16, 1988 now abandoned which was a continuation of Ser. No. 033,657 filed on Apr. 3, 1987 now abandoned.

BACKGROUND OF THE INVENTION

This invention relates to hypodermic needle assemblies of the type suitable for receiving and dispensing medication.

Various types of needle assemblies are known for receiving and dispensing medication. The needle assemblies are typically utilized with a syringe device including a hollow barrel and a plunger positioned within the barrel and operative in response to upward and downward movement of the plunger within the barrel to dispense fluid through the hollow shaft portion of the needle or withdraw fluid upwardly into the barrel through the hollow shaft portion of the needle. The lower end of the shaft portion of the needle is of necessity sharply pointed and as such presents a hazard whenever the point is exposed. Needle assemblies typically include a sheath which is cup shaped and which fits telescopically over the shaft portion of the needle with the upper end of the sheath suitably mounted on the base portion of the needle. In position, the cup shaped sheath totally shields the pointed end of the needle and prevents injury to users of the needle. Prior to use of the needle assembly, the shield is removed from the needle and the needle is utilized in known manner to either dispense medication or receive fluid. The sharp point of the needle is therefore exposed at all times following removal of the safety sheath until the needle assembly is ultimately disposed of, and it is not at all uncommon for puncture wounds to be inflicted by the exposed sharp point of the needle during the time between removal of the sheath and ultimate disposal of the needle assembly. Various devices have been proposed in the past to serve as a shield to protect the needle during and after use but these devices have either been ineffective in terms of performing their shielding function or have been unduly complicated with respect to their construction or their use. In any event, none of these needle shield devices have achieved any significant degree of commercial acceptance because of their ineffectiveness and/or complexity.

SUMMARY OF THE INVENTION

This invention is directed to the provision of a needle assembly in which the sharp point of the needle is protected at all times during and after use of the needle assembly.

The needle assembly of the invention includes an injection needle including a relatively large diameter hollow base portion and a relatively small diameter hollow shaft portion extending downwardly from the base portion and including a lower end portion terminating in a pointed tip; and an elongated unitary sleeve sized to fit telescopically over the needle and including an axially rigid upper mounting portion sized to mount over the needle base portion, an axially collapsible intermediate portion, and an axially rigid lower portion defining an axially extending central bore sized to telescopically receive the needle lower end portion and positioned, with the upper sleeve portion mounted over the needle base portion and the intermediate sleeve portion axially extended, in surrounding relation to the needle end portion with the pointed tip spaced upwardly from the lower end of the bore. With this arrangement, the needle is constantly protected by the sleeve and yet the sleeve yields axially in response to insertion of the needle into the patient or into a suitable aperture to allow the needle to enter the patient without the pointed tip of the needle ever being exposed.

According to a further feature of the invention, the sleeve has a generally uniform diameter throughout its length and the central bore defined in the lower rigid portion the sleeve has a diameter less than the diameter of the needle base portion and greater than the diameter of the needle shaft portion. This arrangement allows the lower end portion of the needle shaft to be positioned telescopically within the central bore of the lower end portion of the sleeve and allows the sleeve to guide on the needle shaft portion as it collapses axially in response to insertion of the needle into an appropriate subject.

In one embodiment of the invention, the needle base portion is externally threaded and the upper mounting portion of the sleeve is internally threaded for threaded coaction with the externally threaded needle base portion. In another embodiment of the invention, the upper mounting portion of the sleeve is sized to be press fit over the needle base portion. In either arrangement, the upper end of the sleeve is conveniently and positively secured to the needle base portion to preclude inadvertant relative movement as between the sleeve and the needle.

According to a further feature of the invention the sleeve has a generally uniform external diameter throughout its length; the upper sleeve portion has an internal diameter approximating the external diameter of the needle base portion; the intermediate sleeve portion is pleated; and the lower sleeve portion has a thickened annular wall and the central bore has a diameter less than the diameter of the needle base portion and greater than the diameter of the needle shaft portion. This specific construction of the sleeve allows the sleeve to fit readily and securely over the needle base portion; allows the intermediate portion of the sleeve to readily collapse to accommodate entry of the needle into a subject; and provides a convenient means of defining the central bore in a sleeve of generally uniform external diameter.

According to a further feature of the invention, the assembly further includes an elongated cup shaped sheath fitted telescopically over the sleeve with its closed lower end positioned intermediately beneath the lower end of the sleeve lower portion and its open upper end positioned concentrically around the needle base portion and the sleeve upper portion. This arrangement allows the sheath of the prior art to be utilized with the sleeve shield of the invention so that the sheath may protect the entire assembly during shipment and storage and the sleeve may protect the pointed tip of the needle following removal of the sheath.

According to a further feature of the invention, the needle assembly further includes a syringe including a hollow cylindrical barrel open at its upper end and secured at its lower end to the needle base portion and a plunger extending into the open upper end of the barrel and including a piston at its lower end for sealing coaction with the barrel to move liquid downwardly from the barrel and downwardly through the needle in response to downward movement of the plunger and move liquid upwardly through the needle and into the barrel in response to upward movement of the plunger. This arrangement allows the invention sleeve shield to be utilized in a typical hypodermic syringe assembly.

BRIEF DESCRIPTION OF THE DRAWINGS

FIG. 1 is a longitudinal cross sectional view of the needle assembly according to the invention;

FIG. 2 is a view of a sleeve for use in the invention needle assembly;

FIG. 3 is an exploded view of the needle assembly of FIG. 1;

FIG. 4 is a longitudinal cross sectional view of the invention needle assembly utilized in a hypodermic syringe assembly; and FIG. 5 is a fragmentary view of the needle assembly of FIG. 3 with a sheath covering the shaft 14 of the needle.

DETAILED DESCRIPTION OF THE PREFERRED EMBODIMENT

The needle assembly seen in FIGS. 1 and 3 includes a needle 10, a sleeve 12, a sheath 14, and a cap 16. Sleeve 12, sheath 14, and cap 16 may be formed of a suitable plastic material in an injection molding process. Needle 10 may be of all metallic construction or may be of a composite plastic and metal construction.

Needle 10 includes a relatively large diameter hollow base portion 10a and a relatively small diameter hollow shaft portion 10b extending downwardly from the base portion and including a lower end portion 10c terminating in a pointed tip 10d. Base portion 10a is preferably formed of a plastic material and includes an upper annular lip 10e and external threads 10f. Needle shaft portion 10b is preferably formed of a suitable metallic material and is secured in known manner to the lower end of base portion 10a.

Sleeve 12 is formed as an injection molded unitary plastic member in a size to fit telescopically over needle 10. Sleeve 12 includes an axially rigid upper mounting portion 12a sized to mount over needle base portion 10a, an axially collapsible intermediate portion 12b, and an axially rigid lower portion 12c defining an axially extending central bore 12d sized to telescopically receive the needle lower end portion 10c and positioned, with upper portion 12a mounted on needle base portion 10a and intermediate portion 12b axially extended, in surrounding relation to needle end portion 10c with the needle pointed tip 10d spaced upwardly from the lower end of bore 12d.

An annular lip 12e is formed at the upper end of upper mounting portion 12a and internal threads 12f are provided in upper portion 12a for threaded coaction with the threads 10f on needle base portion 10a. Intermediate portion 12b is constituted by a series of integral pleats 12g. Pleats 12g have an axially extended normal position, as seen in FIG. 1 in which the individual pleats are axially spaced to provide a sleeve length in which the tip 10d of the needle is positioned within bore 12d of the sleeve in spaced relation to the lower end of the sleeve, and a collapsed position, as seen in FIG. 2, in which the sleeve length is foreshortened by the extent of collapsing axial movement of the intermediate portion to allow selective exposure of the pointed tip of the needle.

The lower sleeve portion 12c has a thickened annular wall 12h defining the central bore 12d and the central bore 12d has a diameter slightly greater than the diameter of needle shaft portion 10b so as to readily slidably receive the shaft portion 10b. Bore 12d fits closely enough around shaft portion 10b so that shaft portion 10b serves as a central guide for the collapsing movement of the sleeve.

Sheath 14 is generally cup shaped and includes a main body cylindrical wall portion 14a, a solid lower end wall 14b, an open upper end 14c, and an annular bead or lip 14d spaced downwardly from open end 14c to define an upper end portion 14e. Sheath 14 is sized to fit telescopically over sleeve 12 and has a length generally corresponding to the length of sleeve 12.

Cap 16 is cup shaped and is sized to fit telescopically over upper end portion 14e of sheath 14.

In assembled relation, as seen in FIG. 1, sleeve 12 is telescopically received over needle 10 with sleeve upper portion 12a threaded onto needle base portion 10a, sleeve lower end portion 12c telescopically receiving and circumferentially surrounding needle lower end portion 10c, and needle tip 10d spaced upwardly from the lower end of sleeve bore 12d; sheath 14 is telescopically received over sleeve 12 with the open upper end 14c of the sheath seating against lip 12e on the upper end of the sleeve and with wall 14b positioned immediately beneath the lower end of sleeve bore 12d; and cap 16 is fitted over the upper end portion 14e of sheath 14 in seating engagement with sheath bead 14d.

The invention needle assembly may be supplied in the form seen in FIG. 1 or, alternatively, may be provided as part of a hypodermic syringe assembly as seen in FIGS. 4 and 5.

The hypodermic syringe assembly of FIGS. 4 and 5 includes a needle 10, a sleeve 12, a sheath 14, and a syringe 18.

Syringe 18 includes a hollow cylindrical barrel 20 and a plunger 22.

Barrel 20 is open at its upper end 20a and includes a hollow mounting hub portion 20b at its lower end.

Plunger 22 is slidably received in barrel 20 and includes a piston 22a for sealing coaction with the inner cylindrical wall of the barrel as the plunger is moved up and down in known manner within the barrel.

The assembly of FIGS. 4 and 5 does not include a cap 16 but, rather, the upper end or base portion 10a of the needle is mounted directly and in known manner in the base portion 20b of the barrel 20 of the syringe. The upper end of sleeve 12 is threaded into abutting engagement with the lower end of barrel hub portion 20b. In the assembled relation as seen in FIG. 4, continuous passage is established from the interior of barrel 20 downwardly through a central bore 20c in the hub portion 20b of the barrel and then downwardly through the hollow needle.

If syringe assembly 18 and a needle assembly of the type seen in FIG. 1 are provided as separate entities, the hypodermic needle assembly is prepared for use by removing the cap 16, inserting the upper end of the needle base portion 10a into barrel hub portion 20b to secure the needle therein in known manner, and removing sheath 14. If the assembly is provided in the form seen in FIG. 4 with the syringe already mounted to the needle, the assembly is prepared for use simply by removing the sheath 14.

In either situation, as pressure is thereafter exerted downwardly on the syringe with the lower end of sleeve 12 positioned against the subject 24 to be treated, the intermediate portion 12b of the sleeve selectively collapses axially as the pointed tip of the needle shaft enters the subject to selectively expose the needle. As the needle is thereafter withdrawn, following either injection of a fluid into the subject or withdrawal of a fluid from the subject, the sleeve 12 selectively expands axially to selectively cover the needle tip as it emerges from the subject so that, the needle tip is never exposed in either the needle entry or needle withdrawal operations. Since most hypodermic assemblies are now of the one use, disposable type, the entire assembly would thereafter immediately be disposed of with the axially extended sleeve continuing to protect the exposed tip of the needle during the disposal process so as to continue to guard against inadvertant injury caused by the exposed needle.

As seen in FIG. 2, the upper rigid portion 12a of sleeve 12 may be provided with a smooth bore, rather than a threaded internal bore, and the upper portion 12a may be press fit on the upper end 10a of needle 10, in which case the external thread 10f on the upper portion 10a of the needle would be omitted to provide a proper press or interference fit as between the upper end of the sleeve and the needle base portion.

The invention will be seen to provide a hypodermic needle assembly in which the point of the needle is protected at all times during and after use to avoid injury caused by the exposed point of the needle. The protective sleeve of the invention is extremely effective in preventing injury from the tip of the needle and yet may be readily and inexpensively manufactured at a cost consistent with the extremely low cost of modern day disposable needle assemblies. In fact, the invention sleeve only insignificantly increases the overall cost of the needle assembly as compared to needle assemblies in which no such protection is provided.

Whereas preferred forms of the invention have been illustrated and described in detail, it will be apparent that various changes may be made in the disclosed embodiments without departing from the scope or spirit of the invention.

I claim:

1. A needle assembly comprising:
   (a) an injection needle including a relatively large diameter hollow base portion and a relatively small diameter hollow shaft portion extending downwardly from said base portion and including a lower end portion terminating in a pointed tip; and
   (b) an elongated unitary sleeve sized to fit telescopically over said needle and including an axially and radially rigid upper mounting portion sized to mount over said needle base portion and including means for coaction with said base portion to detachably secure said sleeve to said base portion, an axially collapsible intermediate portion formed integrally with said upper mounting portion and having a normal extended condition and a collapsed condition to respectively provide a relatively long and a relatively short overall length for said sleeve, and an axially and radially rigid lower portion formed integrally with said intermediate portion and defining an axially extending central bore, of constant length and diameter irrespective of the extended or collapsed condition of said intermediate portion, opening to the atmosphere centrally in the lower end of said sleeve and sized to telescopically but loosely slidably receive said needle lower end portion and positioned, with said upper sleeve portion mounted over said needle base portion and said intermediate portion in its axially extended condition, in surrounding relation to said needle end portion with said pointed tip spaced upwardly from the open lower end of said bore.

2. A needle assembly according to claim 1 wherein:
   (c) said sleeve has a generally uniform diameter throughout its length; and
   (d) said central bore has a diameter less than the diameter of said needle base portion and greater than the diameter of said needle shaft portion.

3. A needle assembly according to claim 1 wherein:
   (c) said needle base portion is externally threaded; and
   (d) said upper mounting portion of said sleeve is internally threaded for threaded coaction with said externally threaded needle base portion to detachably secure said sleeve to said needle base portion.

4. A needle assembly according to claim 1 wherein:
   (c) said upper mounting portion of said sleeve is sized to be press fit over said needle base portion to detachably secure said sleeve to said needle base portion.

5. A needle assembly according to claim 1 wherein:
   (c) said sleeve is formed as an injection molded unitary plastic member and has a generally uniform external diameter throughout its length;
   (d) said upper sleeve portion has an internal diameter approximating the external diameter of said needle base portion;
   (e) said intermediate sleeve portion is pleated; and
   (f) said lower sleeve portion has a thickened annular wall and said central bore has a diameter less than the diameter of said needle base portion and greater than the diameter of said needle shaft portion.

6. A needle assembly comprising:
   (a) an injection needle including a relatively large diameter hollow base portion and a relatively small diameter hollow shaft portion extending downwardly from said base portion and including a lower end portion terminating in a pointed tip;
   (b) and elongated unitary sleeve sized to fit telescopically over said needle and including an axially and radially rigid upper mounting portion sized to fit over said needle base portion and including means for coaction with said needle base portion, to detachably secure said leeve to said needle base portion, an axially collapsible intermediate portion formed integrally with said upper mounting portion and having a normal extended condition and an collapsed condition to respectively provide a relatively long and a relatively short overall length for said sleeve, and an axially and radially rigid lower portion formed integrally with said intermediate portion and defining an axially extending central bore, of constant length and diameter irrespective of the extended or collapsed condition of said intermediate portion, opening to the atmosphere centrally in the lower end of said sleeve and sized to telescopically but loosely slidably receive said needle lower end portion and positioned, with said upper portion mounted over said needle base portion and said intermediate portion in its axially extended condition, in surrounding relation to said needle lower end portion with said pointed tip spaced upwardly from the open lower end of said bore; and
   (c) an elongated cup shaped sheath fitted telescopically over said sleeve and having an imperforate, closed lower end positioned immediately beneath the lower end of said sleeve lower portion and an open upper end positioned concentrically around said needle base portion and said sleeve upper portion.

7. A needle assembly according to claim 6 wherein:
(d) said sleeve has a generally uniform diameter throughout its length; and
(e) said central bore has a diameter less than the diameter of said needle base portion and greater than the diameter of said needle shaft portion.

8. A needle assembly according to claim 7 wherein:
(e) said needle base portion is externally threaded; and
(f) said upper mounting portion of said sleeve is internally threaded for threaded coaction with said externally threaded needle base portion to detachably secure said sleeve to said needle base portion.

9. A needle according to claim 7 wherein:
(e) said upper mounting portion of said sleeve is sized to be press fit over said needle base portion to detachably secure said sleeve to said needle base portion.

10. A needle assembly according to claim 6 wherein:
(d) said sleeve has a generally uniform external diameter throughout its length;
(e) said upper sleeve portion has an internal diameter approximating the external diameter of said needle base portion; and
(f) said lower sleeve portion has a thickened annular wall and said central bore has a diameter less than the diameter of said needle base portion and greater than the diameter of said needle shaft portion.

11. A needle assembly comprising:
(a) an injection needle including a relatively large diameter hollow base portion and a relatively small diameter hollow shaft portion extending downwardly from said base portion and including a lower end portion terminating in a pointed tip;
(b) an elongated unitary sleeve sized to fit telescopically over said needle and including an axially and radially rigid upper mounting portion sized to fit over said needle base portion and including means for coaction with said needle base portion to detachably secure said sleeve to said needle base portion, an axially collapsible intermediate portion formed integrally with said upper mounting portion and having a normal extended condition and a collapsed condition to respectively provide a relatively long and relatively short overall length for said sleeve, and an axially and radially rigid lower portion formed integrally with said intermediate portion and defining an axially extending central bore, of constant length and diameter irrespective of the extended or collapsed condition of said intermediate portion opening to the atmosphere centrally in the lower end of said sleeve and sized to telescopically but loosely slidably receive said needle lower end portion and positioned, with said upper portion mounted over said needle base portion and said intermediate portion in its axially extended condition, in surrounding relation to said needle lower end portion with said pointed tip spaced upwardly from the open lower end of said bore;
(c) an elongated cup shaped sheath fitted telescopically over said sleeve and having an imperforate, closed lower end positioned immediately beneath the lower end of said sleeve lower portion and an open upper end positioned concentrically around said needle base portion and said sleeve upper portion; and
(d) a syringe including a hollow cylindrical barrel open at its upper end and secured at its lower end to said needle base portion and a plunger extending into the open upper end of said barrel and including a piston at its lower end for sealing coaction with said barrel to move liquid downwardly from said barrel and downwardly through said needle in response to downward movement of said plunger and move fluid upwardly through said needle into said barrel in response to upward movement of said plunger.

12. A needle assembly according to claim 11 wherein:
(e) said sleeve has a generally uniform diameter throughout its length; and
(f) said central bore has a diameter less than the diameter of said needle base portion and greater than the diameter of said needle shaft portion.

13. A needle assembly according to claim 11 wherein:
(e) said needle base portion is externally threaded; and
(f) said upper mounting portion of said sleeve is internally threaded for threaded coaction with said externally threaded needle base portion to detachably secure said sleeve to said needle base portion.

14. A needle assembly according to claim 11 wherein:
(e) said upper portion of said sleeve is sized to be press fit over said needle base portion to detachably secure said sleeve to said needle base portion.

15. A needle assembly according to claim 11 wherein:
(e) said sleeve has a generally uniform external diameter throughout its length;
(f) said upper sleeve portion has an internal diameter approximating the external diameter of said needle base portion;
(g) said intermediate sleeve portion is pleated; and
(h) said lower sleeve portion has a thickened annular wall and said central bore has a diameter less than the diameter of said needle base portion and greater than the diameter of said needle shaft portion.

16. A needle assembly according to claim 6 and further including:
(d) a cup shaped cap fitted telescopically over the upper end portion of said sheath and concentrically around said needle base portion and said sleeve upper portion.

17. A needle assembly comprising:
(A) an injection needle including a relatively large diameter hollow upper portion, having an open upper end, and a relatively small diameter hollow shaft portion extending downwardly from said upper portion and including an lower end portion terminating in a pointed tip;
(B) an elongated unitary sleeve sized to fit telescopically over said needle and including a rigid upper mounting portion sized to mount over said needle upper portion and including means for coaction with said upper portion to detachably secure said sleeve to said upper portion, an axially collapsible intermediate portion formed integrally with said upper mounting portion and having a normal extended condition and a collapsed condition to selectively provide a relatively long and a relatively short overall length for said sleeve, and a rigid lower portion formed integrally with said intermediate portion and defining an axially extending central bore opening to the atmosphere centrally in the lower end of said sleeve and sized to telescopically receive said needle lower end portion and positioned, with said upper sleeve portion mounted over said needle upper portion and said intermediate portion in its axially extended condition, in surrounding relation to said needle end portion with said pointed tip spaced upwardly from the open lower end of said bore; and (c) sealing means including a seal member separate from said sleeve member and said needle member, including a portion extending beneath said sleeve member lower portion in underlying but unattached relation to the lower end of said sleeve, coacting with at least one of said sleeve and needle members to preclude the entry of contaminants into the open lower end of said bore, and readily removably from said sleeve member and said needle member to allow said pointed tip to pass freely through the open lower end of said bore.

18. A needle assembly according to claim 17 wherein said sealing means further includes means overlying the open upper end of said needle member upper portion and coacting with at least one of said members to preclude the entry of contaminants into the open upper end of said upper portion of said needle member.

19. A seal assembly according to claim 17 wherein said seal member comprises a tubular member received telescopically over said sleeve member, detachably secured at its upper end to said sleeve member upper portion, and including an imperforate lower end wall underlying said open lower end of said bore.

20. A needle assembly according to claim 19 wherein said sealing means includes a further sealing member positioned in overlying relation to the open upper end of said needle member upper portion, detachably secured to at least one of said members, and coacting with at least one of said members to preclude the entry of contaminants into the open upper end of said needle member upper portion.

21. A needle assembly according to claim 20 wherein said further sealing member comprises a tubular member received telescopically over said upper portion of said needle member, detachably secured at its lower end to one of said members, and including an imperforate upper end wall overlying the open upper end of said needle member upper portion.

* * * * *